(12) United States Patent　　(10) Patent No.:　　US 8,114,084 B2
Betts　　(45) Date of Patent:　　Feb. 14, 2012

(54) EXPANDABLE BLADE DEVICE FOR STABILIZING COMPRESSION FRACTURES

(75) Inventor: Andres Betts, San Clemente, CA (US)

(73) Assignee: Vertech, Inc., San Clemente, CA (US)

( * ) Notice: Subject to any disclaimer, the term of this patent is extended or adjusted under 35 U.S.C. 154(b) by 608 days.

(21) Appl. No.: 11/836,731

(22) Filed: Aug. 9, 2007

(65) Prior Publication Data

US 2008/0221608 A1　Sep. 11, 2008

Related U.S. Application Data

(60) Provisional application No. 60/893,556, filed on Mar. 7, 2007.

(51) Int. Cl.
*A61B 17/00* (2006.01)
*A61B 17/58* (2006.01)
*A61B 17/60* (2006.01)
*A61F 2/46* (2006.01)
*A61F 2/00* (2006.01)

(52) U.S. Cl. ............. 606/79; 606/86 R; 606/95

(58) Field of Classification Search ............ 606/79, 606/80, 86 R, 95
See application file for complete search history.

(56) References Cited

U.S. PATENT DOCUMENTS

| | | | | |
|---|---|---|---|---|
| 5,275,610 A * | 1/1994 | Eberbach | ....... | 606/198 |
| 5,591,170 A * | 1/1997 | Spievack et al. | ....... | 606/82 |
| 5,678,572 A * | 10/1997 | Shaw et al. | ....... | 128/899 |
| 6,916,308 B2 * | 7/2005 | Dixon et al. | ....... | 604/122 |
| 7,396,357 B2 * | 7/2008 | Tornier et al. | ....... | 606/91 |

* cited by examiner

*Primary Examiner* — Thomas C. Barrett
*Assistant Examiner* — David Bates
(74) *Attorney, Agent, or Firm* — Fish & Associates, PC

(57) ABSTRACT

The present invention relates generally to medical devices and medical methods, in particular, devices and methods useful for stabilizing compression fractures of the spine. In one embodiment, the present invention is a device comprising a housing having a lumen; a plunger having a proximal portion and a distal portion, where the plunger is disposed within the lumen and is movable relative to the housing; a plurality of blades, where the blades can expand radially from the axis of the housing; and a manipulator functionally connected to the plunger, wherein the manipulator is operable to: move the plunger relative to the housing; expand the blades radially from the axis of the housing; and move the blades about the axis of the plunger.

12 Claims, 3 Drawing Sheets

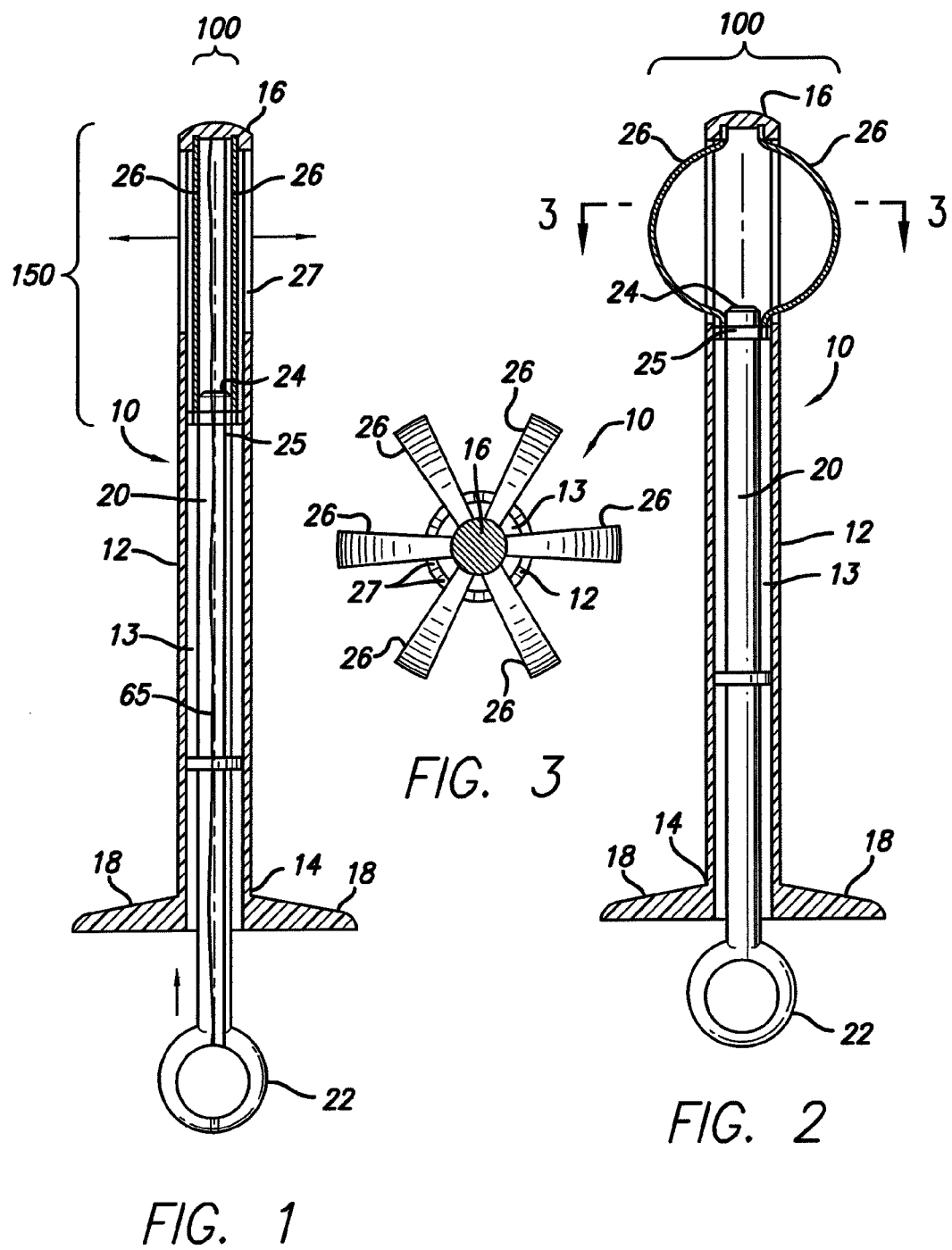

EXPANDABLE BLADE DEVICE FOR STABILIZING COMPRESSION FRACTURES

CROSS-REFERENCE TO RELATED APPLICATION

This application claims priority to provisional patent application Ser. No. 60/893,556, filed on Mar. 7, 2007, which is hereby incorporated by reference in its entirety.

FIELD OF THE INVENTION

The present invention relates generally to medical devices and medical methods. More particularly, the present invention relates to devices and methods useful for stabilizing compression fractures of the spine.

BACKGROUND OF THE INVENTION

Compression fractures of the spine are a common, painful, and debilitating complication of osteoporosis or neoplastic diseases of the vertebral bodies. In many patients, the pain is very severe and patients are unable to bear their own weight. This can require prolonged bed rest, which is known to lead to further complications including pneumonia, thromboembolism, muscle-wasting, and further bone demineralization. In addition to being painful and debilitating, compression fractures of vertebral bodies also typically result in a loss of vertebral height along the anterior margin of the involved vertebrae. This leads to an anterior wedge deformity that causes the kyphosis. Patients having compression fractures of the spine are generally treated by a procedure called percutaneous Vertebroplasty.

Vertebroplasty procedures involve the delivery of polymethylmethacrylate (PMM) cement into the body of the fractured vertebra. The procedure utilizes fluoroscopically-guided percutaneous insertion of large bore hollow cannulas into the anterior portion of the involved vertebra. The tip of the cannula is then carefully maintained within the marrow cavity. Once positioned, PPM cement, containing premixed barium to allow for fluoroscopic visualization, is instilled through the cannula. The cement material binds to the internal trabecular bone structure, resulting in stabilization of the fracture and pain relief.

Vertebroplasty has been widely used. Unfortunately, however, the procedure results in very little to no change in the vertebral height or correction of the associated kyphotic deformity. A recent study suggests that uncorrected kyphosis can lead to chronic pain despite treatment of the fracture itself. In addition, the Vertebroplasty procedure allows for very little control of the direction of the instilled PPM cement. This lack of control can lead to extra-osseous extravasation, including intravascular injection. The lack of control in the Vertebroplasty procedure can even lead to the cement straying into the spinal canal and causing nerve or spinal cord damage.

An alternate form of Vertebroplasty that addresses this kyphosis problem has been developed in the prior art as well. Similar to standard Vertebroplasty, Kyphoplasty involves the placement of a large bore cannula; however, prior to cement delivery, a balloon tamp is inserted into the vertebral body. The balloon tamp is then inflated with a contrast media that compresses the trabecular bone within the fractured vertebra, thereby creating a void. The tamp is subsequently deflated and PMM cement is instilled. Due to the void created by the balloon, the cement preferentially flows into the preformed vertebral body cavity. Additionally, the balloon may be inflated so as to controllably deflect the superior endplate in a cephalad direction. By doing so, the height of the affected vertebra may be restored, thereby correcting the kyphotic deformity associated with the compression fracture.

One potential disadvantage of Kyphoplasty, however, is that the compression of the vertebral trabecular bone by the bone tamp typically results in the formation of a pseudo-membrane around the deposited cement. The pseudo-membrane formed by Kyphoplasty prevents a true cement/trabecular bone interface from occurring. A recent study of the biomechanical integrity of such a vertebral body that has undergone a Kyphoplasty cement augmentation demonstrates that the cortical bone surrounding the deposited cement has a weaker mechanical profile than bone augmented by Vertebroplasty, where the cement is able to interdigitate with the trabecular bone. This study showed that a significant amount of vertebra height that is originally restored with Kyphoplasty is subsequently lost with mechanical loading of the vertebrae. This is further supported by a clinical study that demonstrated a progressive loss of vertebral height among patients that underwent a previous successful Kyphoplasty. As such, it appears that unless the cement is able to interdigitate with the trabecular bone, the height restoration achieved by Kyphoplasty cannot be sustained.

Another potential disadvantage of Kyphoplasty is the use of contrast material in the balloon tamp to allow for fluoroscopic visualization during the procedure. If the balloon were to rupture, the contrast material spillage may cause allergic reactions in susceptible patients.

An alternative method of displacing the trabecular bone, known as the Arcuate™ system, has been developed by Medtronics, Inc. This system utilizes a single curved blade that can be erected to perform an internal osteotomy within the trabecular bone, as opposed to the crushing method of Kyphoplasty. The blade is an arc of thin metal that acts to cut an internal osteotomy in the trabecular bone by turning of the handle, thus allowing for the PMM cement to preferentially collect osteotomized region. The single blade design is able to carve a space within the vertebra; however, it is difficult to accurately position the device under the superior endplate using fluoroscopic monitoring due to parallax and the limits of a two-dimensional projection of a single three-dimensional curve.

Furthermore, the Arcuate™ system only has two settings for the blade position, thereby limiting the adjustments available that would be necessary for the wide range of vertebral body dimensions. The larger blade height may be too large for a given vertebra, potentially resulting in the rupture of the endplate. Additionally, the two-step ratchet mechanism of the Arcuate™ system does not allow for tactile feedback to the operator. Also, the maximal height contour of the blade is at the proximal end of the curve and cannot be positioned anteriorly, where the vertebral body wedge deformity is located. Instead, the maximal height of the blade occurs in the mid to posterior aspect of the vertebral body, distant from the anterior portion of the endplate where the kyphosis is localized. As such, this system is limited to only forming an internal osteotomy within the vertebral trabecular bone, and is not suited to actual vertebral height augmentation.

SUMMARY OF THE INVENTION

The present invention relates to devices and methods useful for stabilizing compression fractures of the spine. More particularly, the present invention relates to devices utilizing a plurality of expandable blades and methods of using such devices.

In one embodiment, the present invention is a device comprising a housing having a lumen; a plunger having a proximal portion and a distal portion, where the plunger is disposed within the lumen and is movable relative to the housing; a plurality of blades located at the distal portion of the plunger, where the blades are operable to: expand radially from the axis of the housing; reduce the volume trabecular bone; and exert force radially; a manipulator functionally connected to the plunger, wherein the manipulator is operable to: move the plunger relative to the housing; expand the blades radially from the axis of the housing; and move the blades about the axis of the plunger. In some embodiments, the device has six blades. In other embodiments, the device has two blades. In some embodiments, force exerted on the blades is transferred to the manipulator. In certain embodiments, the plunger is flexible. In some embodiments, the blades expand to a plurality of diameters.

In some embodiments, a method of the present invention involves the stabilization of a fractured vertebra and the restoration of the height of the fractured vertebra. A method of the invention includes the steps of accessing the internal volume of a vertebral body; inserting a device into the internal volume; restoring the height of the superior endplate of the vertebral body to a normal anatomical position, using the device; reducing the volume of the trabecular bone within the vertebral body, using the device; instilling a biological binding material into the internal volume of the vertebral body, where the amount of the biological binding material instilled is sufficient to add stability to the vertebral body. In some embodiments, the device has a plurality of blades that expand radially from a first position to a second position. In some embodiments, the device is a device as described herein. According to the invention, the restoring step includes expanding the plurality of blades thereby displacing the superior endplate to a normal anatomical position. In some embodiments, the reducing step includes manipulating the plurality of blades to cut trabecular bone within the vertebral body to create a space in the vertebral body. In certain embodiments the biological binding material is PMM cement. In some embodiments the biological binding material interdigitates with trabecular bone in the internal volume of the vertebral body. The method may further include monitoring the movement of the device by fluoroscopic imaging. In some embodiments the accessing step uses a percutaneous method. In various embodiments, the vertebral body is accessed in a similar fashion to the prior art methods, that is, with a large bore cannula through the pedicle.

In some embodiments the present invention is a kit including a device as described herein; a large-bore cannula; a PMM cement; and a device operable to deliver the PMM cement to an internal volume of a bone.

Alternatively, in certain fractures where a plate and screw system is employed in the fracture repair approach, the intramedullary PMM cement may be instilled prior to placement of plate and/or screws. When the PMM cement is allowed to harden the screws may be placed in the usual fashion but will be securely anchored into the predelivered PMM cement, rather than osteoporotic bone.

In addition, in cases wherein osteoporotic patients who are to undergo vertebral fusion procedures with pedicle screw fixation, the practice of pre-instillation of PMM cement into the vertebra may serve to better anchor the pedicle screws to prevent screw dislodgement.

BRIEF DESCRIPTION OF THE DRAWINGS

FIG. 1 is a partial cross-sectional view of an embodiment of a device of the present invention with its blades in a retracted position.

FIG. 2 is a partial cross-sectional view of the embodiment depicted in FIG. 1.

FIG. 3 is a top-down view of the embodiment depicted in FIG. 2.

DETAILED DESCRIPTION

Figure 4:
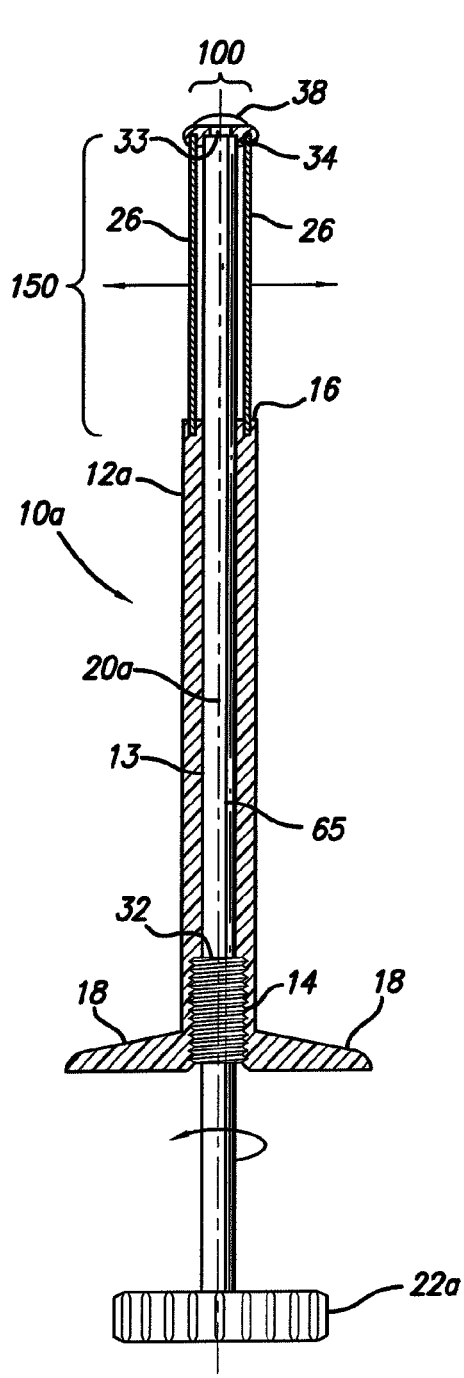
FIG. 4 is a partial cross-sectional view of an embodiment of a device of the present invention.

In the following paragraphs, the present invention will be described in detail by way of example with reference to the attached figures. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

A. Devices of the Present Invention

Referring now to the figures, which are illustrative of multiple embodiments of the present invention only and are not for purposes of limiting the same, FIG. 1 depicts an expandable blade device 10 constructed in accordance with one embodiment of the present invention. The expansion blade device includes a rigid housing 12 which defines a lumen 13. Preferably the housing 12 is roughly tubular, but it may be any suitable shape or configuration. Housing 12 may be any suitable material, such as a suitable polymer, plastic, metal or alloy. In some embodiments, housing 12 may be flexible. The lumen 13 is preferably tubular, but it may be any suitable shape or configuration. In preferred embodiments, the device 10 of the present invention is insertable within a cannula 60 which has been placed within the injured vertebra. Preferably, cannula 60 is a large bore cannula between about eight gauge to about eleven gauge.

The housing 12 has a proximal end 14 and a distal end 16. Preferably, distal end 16 is closed. In some embodiments, proximal end 14 includes grip member 18 that may aid a user's ability to grip and/or manipulate device 10. In some embodiments, grip member 18 is located at proximal end 14, but grip member 18 may be located near proximal end 14 or at any suitable position on housing 12. In the depicted embodiment, grip member 18 is a pair of wings where each wing extends outwardly from proximal end 14 in opposed relation to the other. In such an embodiment, a user's index finger may be placed over one of the wings comprising grip member 18, while the user's middle finger may be placed over the other wing comprising grip member 18, similar to the handling of a syringe. In other embodiments, grip member 18 may be any suitable structure that may aid user's ability to grip and/or manipulate device 10, for example finger loops, depressions, grooves, or a textured surface.

As illustrated in FIGS. 1 and 2, plunger 20 is disposed within the lumen 13 of housing 12 such that plunger 20 is movable relative to housing 12. Similar to housing 12 and lumen 13, plunger 20 may be any suitable diameter and length. In preferred embodiments, plunger 20 has a diameter slightly less than lumen 13 such that plunger 20 is movable along the axis of the housing, but exhibits little, if any, movement transverse to the axis of the housing. In some embodiments, plunger 20 may be equipped with a structure or structures that facilitate its movement within the lumen 13. In some embodiments, plunger 20 may be flexible.

A manipulator 22 is located at or near the proximal end of plunger 20. Manipulator 22 may be any structure suitable to permit the user to move plunger 20 relative to housing 12. In some embodiments manipulator 22 may be a loop, a lever, handle, or dial. In preferred embodiments, manipulator 22 is connected, directly or indirectly, to plunger 20 and blades 26 such that force acting upon blades 26 is transferred to manipulator 22. Accordingly, in preferred embodiments, the user of device 10 is provided with a tactile feel.

Attached to the distal portion of plunger 20 is a plurality of blades 26. The use of multiple blades, as opposed to a single blade, allows for more surface area to contact the vertebral endplate and promotes more reliable fluoroscopic imaging in multiple planes. Each blade 26 may have any suitable width and each blade 26 in a given device need not have the same width. In some embodiments the blades 26 may have a width of from about 0.5 mm to about 10 mm. Preferably, each blade 26 has a width of from about 2 mm to about 3 mm. The blades 26 are disposed substantially parallel to the axis of housing 12 and, in their unexpanded stated, do not protrude past the outer surface of housing 12. Each blade 26 may be composed of any suitable material that can cut or shave trabecular bone and is resilient. In some embodiments, blades 26 may be made of any compliant polymer, plastic, metal or alloy. Preferably, blades 26 are made of metal. Embodiments of the invention may feature any number of blades 26. In some embodiments there may be 2, 3, 4, 5, 6, 7, 8, 9, or 10 blades. In a preferred embodiment, there are six blades 26. In another preferred embodiment, there are two blades 26.

In some embodiments, the distal portion of housing 12 has a plurality of slots 27. Preferably the slots 27 are located close to the distal end 16. The slots 27 may be any shape and size so long as they do not impede radial expansion of the blades 26. In the illustrated embodiment, the slots 27 are elongate rectangular in shape.

Blades 26 are disposed such that when manipulator 22 is moved in a certain manner, the blades 26 will expand radially from the axis of the housing. In some embodiments, this is achieved by translating the distal movement of plunger 20 along the axis of housing 12, for example as depicted in FIG. 2, in to the expansion or flexing of blades 26 radially away from the axis of the housing 12 and through slots 27. In the illustrated embodiments such movement is achieved by attaching the proximal ends of blades 26 to plunger 20 and attaching the distal ends to housing 12. Blades 26 may be attached to plunger 20 and housing 12 in any suitable manner, including indirectly. In some embodiments, blades 26 may be attached by welding, crimping, screws, rivets, or adhesives. The blades 26 may be attached to any suitable location of the plunger 20 and housing 12. Preferably, the proximal ends of blades 26 are attached in proximity to the distal end 24 of plunger 20 and the distal ends of blades 26 are attached to an interior surface of the housing 12 at the distal end 16. In a preferred embodiment, the proximal ends of blades 26 are each attached to a shoulder portion 25 of the plunger 20 which is located proximally to the distal end 24 of plunger 20.

The disposition of the blades 26 is also such that a diameter 100 of the blades 26 in the expanded configuration is variable. FIG. 1 illustrates an embodiment where blades 26 are not expanded radially outward, whereas FIG. 2 illustrates an embodiment that where the blades 26 are expanded to the maximum diameter. Although not depicted, the user may vary the extent of the expansion of the blades 26 and thereby vary the diameter 100 between the maximum and the unexpanded states. The user varies the diameter by varying the movement of the plunger 20 relative to the housing. The user may control this movement by acting upon the manipulator 22 and moving the manipulator 22 with respect to grip member 18. Accordingly, for example, in FIGS. 1 and 2 the user's movement of the manipulator 22 toward the distal end 16 of housing 12 moves plunger 20 toward the distal end 16 of housing 12. In turn, the movement of plunger 20 moves the proximal end of blade 26 toward the distal end of blade 26, thereby expanding blade 26 radially from the axis of housing 12. FIG. 3 depicts device 10 from a top-down perspective, with the blades 26 being in a fully deployed state illustrated in FIG. 2. As is illustrated in FIG. 3, each blade 26 protrudes through a slot 27 disposed within the rigid housing 12. In some such embodiments, the distance of the movement of plunger 20 toward the distal end of housing 12 controls the amount of expansion of blade 26 and the diameter 100. In a preferred embodiment, the maximum diameter between blades is about 2 cm. In some embodiments manipulator 22 is configured to display or otherwise notify the user of the cutting diameter of the blades 26. For example, manipulator 22 or the distal portion of plunger 20 may have markings showing the extent of radial expansion of blades 26 achieved by a certain movement of manipulator 22.

Due to the resiliency and shape memory properties of blades 26, once expanded, the blades have a tendency to return to their unexpanded position depicted in FIG. 1. Accordingly, in some embodiments, the blades 26 remain expanded only so long as the user applies force to the manipulator 22 (and thereby to plunger 20). In other embodiments, the manipulator 22 is configured such that the user need not apply continuous force to maintain the expansion of blades 26. In some such embodiments, the blades 26 may be maintained in a fully or partially expanded state through the use of a clamp, or some other fastening means (not shown) that is operable to maintain the plunger 20 in a prescribed position relative to the housing 12.

In some embodiments, device 10 may also have a guide wire engaging member 65 that functions to engage a structure that aids the insertion or other movement of device 10 within the body. In some embodiments, the guide wire engaging member 65 is a hollow in device 10 extending from its distal end 16 to the manipulator 22 (as depicted in FIG. 1). In such an embodiment, plunger 20 would have a hollow, as would manipulator 22 and distal end 16.

Figure 5:
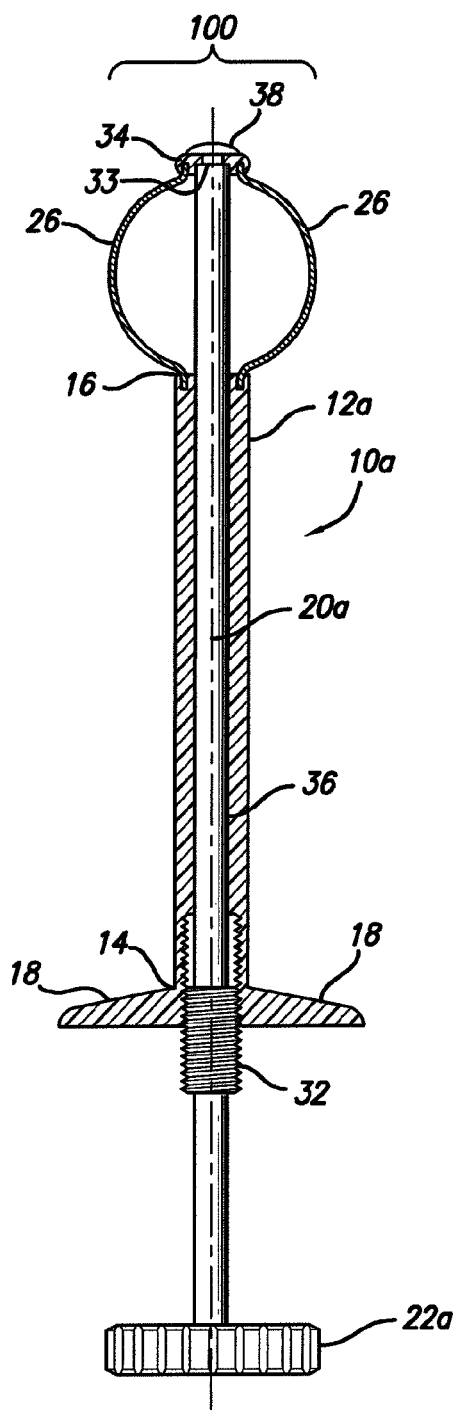
FIG. 5 is a partial cross-sectional view of the embodiment depicted in FIG. 4.

FIGS. 4 and 5 depict an alternative embodiment of a device of the present invention, device 10a. Similarly to the device 10 depicted in FIGS. 1 and 2, device 10a comprises a housing 12a having a proximal end 14 and a distal end 16, a grip member 18 (depicted as a pair of wings), lumen 13 and blades 26. Device 10a may also have guide wire engaging member 65 (as illustrated in FIG. 4). The depicted embodiment works in a manner similar to the embodiment depicted in FIGS. 1 and 2, but, among other differences, utilizes a manipulator 22a, housing 12a, and configuration of plunger 20a that are different than those in the embodiment depicted in FIGS. 1 and 2.

In the embodiment depicted in FIGS. 4 and 5, a proximal portion of the interior surface of the housing 12a has a threaded region 36. Similarly, a proximal portion of plunger 20a has a threaded region 32. The threaded portion 32 is threadably engaged to the internally threaded portion 36 of the housing 12a. As such, rotation of plunger 20a causes movement of plunger 20a along the axis of housing 12a. Housing 12a does not extend to the distal end of the device 10a in this embodiment. Distal end 16 is near the proximal end of blades 26. Blades 26 are attached at their proximal end to housing 12a and at their distal end to sleeve 34. Sleeve 34 is rotatably connected to plunger 20a is an annular sleeve 34 which partially resides within a continuous, circumferentially extending groove 33 which is disposed in close proximity to distal end 38 of plunger 20a. Sleeve 34 is capable of rotation relative to the screw unit 28 when the plunger 20a is rotated relative to the housing 12a.

Manipulator 22a in the depicted embodiment is a handle portion that extends radially from the axis of housing 12a. In this embodiment, manipulator 22a is configured to allow the user to grasp and rotate manipulator 22a and, thereby rotate plunger 20a. Of course, manipulator 22a can have any configuration capable of rotating plunger 20a relative to housing 12a. In the depicted embodiment, blades 26 are extended by counter-clockwise rotation of manipulator 22a which, in turn, causes counter-clockwise rotation of plunger 20a relative to housing 12a. In such an embodiment, the counter-clockwise rotation of manipulator 22a moves manipulator 22a away from the housing 12a, thereby causing plunger 20a to move proximally along the axis of housing 12a. Such movement decreases the distance between the distal end 16 of housing 12a and the distal end 38 of plunger 20a to decrease. Since the blades 26 are resilient and flexible and attached to the distal end 38 of plunger 20a and near the distal end 16 of housing 12a, this decrease in distance forces the blades 26 to expand or flex (and hence deploy) radially from the axis of housing 12a in the manner illustrated in FIG. 5. Conversely, in the depicted embodiment, when manipulator 22a and plunger 20a are rotated in a clockwise direction, the distance between the distal ends 16 and 38 is effectively increased, causing the blades 26 to return to the initial, unexpanded position illustrated in FIG. 4. Like in device 10, the blades 26 of device 10a may be partially expanded or deployed to a state lying anywhere between the extremes illustrated in FIGS. 4 and 5 by selective variation in the degree of rotation of manipulator 22a. Of course, one of skill in the art will appreciate that the device could be configured such that counter-clockwise movement contracts the blades 26 and clockwise movement expands the blades 26.

In some embodiments, the configuration of the screw mechanism is such that blades 26 will remain in a particular expanded state even though the user is not applying force to manipulator 22a. Accordingly, the blades 26 can be maintained in the deployed position without continuous application of force by the user and without the need for any ancillary clamping or similar device. In such embodiments blades 26 will remain until plunger 20a is rotated in a clockwise manner until the blades 26 are returned to their initial unexpanded position.

In those instances when the user wants to rotate device 10 in its entirety, the user may simultaneously rotate the housing 12a and plunger 20a. In another embodiment, such rotation may be assisted through the use of a clamp (not shown), or other fastening device or configuration operative to lock plunger 20a in place relative to the housing 12a. In this case, when the clamp is locked, device 10a may be rotated in its entirety by either rotating the plunger 20a (or manipulator 22a) or the housing 12a, without the user ensuring that the two are simultaneously rotating.

B. Methods of the Present Invention

In addition to the devices described above, the present invention also includes methods of using the devices of the present invention and any other suitable device.

Figure 6:
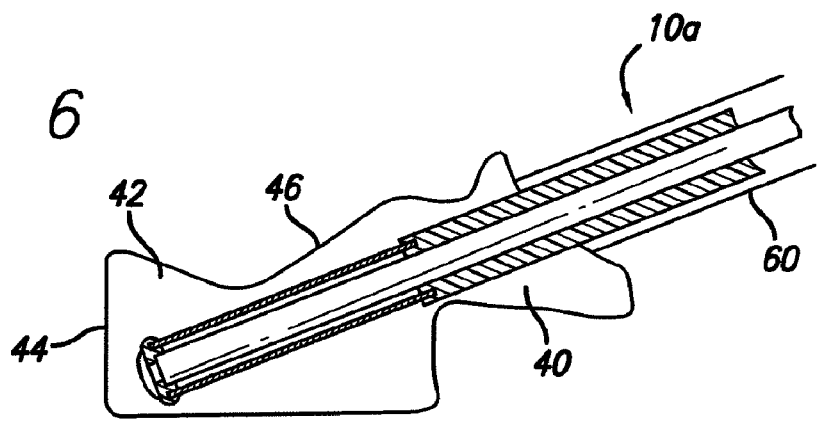
FIG. 6 is a partial side view illustrating an exemplary positioning of an embodiment of a device of the present invention within the vertebral body, wherein the blades of the device are in a retracted position.
Figure 7:
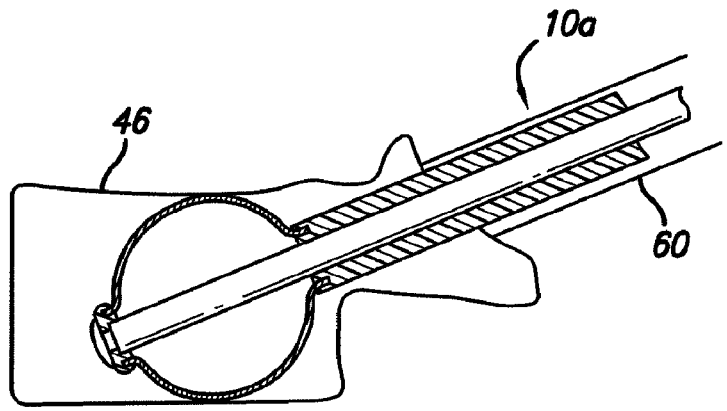
FIG. 7 is a partial side view illustrating the positioning of an embodiment of a device of the present invention, wherein the blades are in a deployed position and the vertebral height as been restored.
Figure 8:
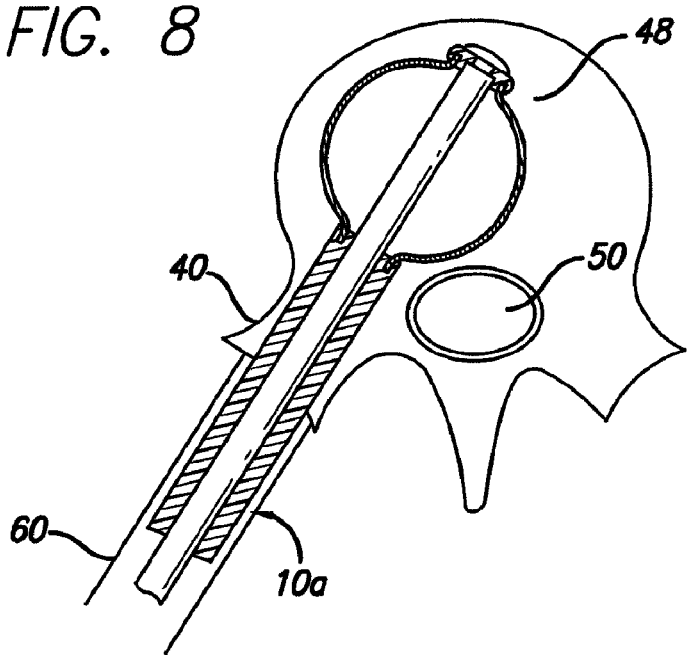
FIG. 8 is a top-down view of an exemplary positioning of an embodiment of a device of the present invention within the vertebral body, wherein the device entered the vertebral body via the pedicle while avoiding the spinal canal.

FIGS. 6-8 depict an embodiment of a method of the present invention useful to stabilize a vertebra fracture while also restoring the vertebral height. As depicted, the method uses device 10a, but any suitable device may be used, including device 10 and any other embodiment of the devices of the present invention.

The method initially involves getting access to the interior volume of vertebral body 42. In some embodiments, this is done by percutaneously inserting a cannula 60. In other embodiments, an open procedure may be used to get access to the interior volume of vertebral body 42. Cannula 60 may be any structure suitable for providing access to vertebral body 42 and can be made of any suitable material. Preferably, cannula 60 is a hollow tube having a diameter slightly larger than the diameter of the device used in the procedure. In any event, the exterior surface of vertebral body 42 is drilled, cut, or otherwise compromised to permit access to the internal volume. Such may be achieved by any suitable method and with any suitable device.

The interior volume of vertebral body 42 can be accessed at any suitable position. In some embodiments, access may be through a side of vertebral body 42. In other embodiments, access may be through the posterior of vertebral body 42. In preferred embodiments, access to the internal volume of vertebral body 42 is through the pedicle 40. As depicted in FIG. 8, by inserting cannula 60 into the vertebra body 42 through the pedicle 40, the user is better able to avoid penetrating the spinal canal 50, thereby preventing potentially permanent damage and paralysis to the patient. In some embodiments, the location of cannula 60 may be visualized by any suitable imaging technique, including those known in the art. Preferably, visualization is by fluoroscopic imaging techniques.

After gaining access to the internal volume of vertebral body 42, device 10a is inserted into that internal volume. In preferred embodiments, device 10a is inserted into and advanced through cannula 60. In preferred embodiments, device 10a is inserted into the cannula with the blades 26 in an unexpanded state. In other embodiments, blades 26 may be expanded to some extent, so long as blades 26 do not prevent insertion of the device 10a into cannula 60 or into vertebral body 42. The device 10a is advanced through the cannula so that the blades 26, 26 protrude beyond the distal end of the cannula 60 and into the internal volume of vertebral body 42. In preferred embodiments, device 10a is moved or manipulated until blades 26 are near the anterior surface 44 of the vertebra body 42, as depicted in FIG. 6. In some embodiments, the extent of insertion of device 10a is monitored using a suitable imaging technique.

When the device 10a is properly positioned within the vertebral body 42, the blades 26 are expanded radially as needed to contact superior endplate 46. The expansion of the blades 26 may be done by any method, including those described herein. For example (and with reference to FIGS. 4 and 5), in the case of device 10a, the blades 26 may be expanded by rotating manipulator 22a counter-clockwise relative to housing 12a, thereby causing plunger 20a to rotate counter-clockwise and decreasing the distance between the distal ends 16, 38. Blades 26 are expanded such that they apply force to superior endplate 46 until the superior endplate 46 has been displaced into a desired position. In preferred embodiments, the desired position for superior endplate 46 is the normal anatomical position for the particular patient, for example as depicted in FIG. 7. Although the normal anatomical position of superior endplate 46 may be different for each patient or even each vertebrae of each patient, a preferred method, which will properly position the superior endplate 46 for many patients, contemplates expanding blades 26 to a diameter of about 2 cm.

In a preferred embodiment, the blades 26 are made of metal and are easily visualized using fluoroscopic methods. However, various other imaging techniques and methods, some capable of visualizing blades 26 that are not made of metal, may be used in other embodiments. However achieved, visualization of the blades 26 aids the user in expanding blades 26 as needed to achieve the desired orientation of the superior endplate 46. Visualization may also aid the user in performing other aspects of the methods of the present invention. In some embodiments, the force of contact between blades 26 and superior endplate 46 is transmitted to the user of device 10*a* through the manipulator. In some such embodiments, this tactile feel aids the user in determining if and when superior endplate has been moved to the desired position. In further embodiments the immediate tactile feedback provided to the user is combined with the visual fluoroscopic imaging, resulting in restoration of the vertebral height with minimal risk of rupturing the vertebral body itself.

Expansion of the blades is also necessary for another aspect of the methods of the present invention that may be performed before or after the superior endplate 46 is restored—cutting, carving, shaving, or otherwise reducing the volume of the trabecular bone 48 in the internal volume of vertebral body 42. In preferred embodiments, the trabecular bone 48 is cut, carved, or shaved, preferably in a manner that leaves the trabecular bone with texture and/or pores that may receive a biological binding material. In a preferred embodiment once the blades 26 are expanded and the superior endplate 46 has been restored to the desired position, device 10*a* is rotated in its entirety to carve out the trabecular bone 48 within the vertebral body 42, thereby creating a void within the internal volume of the vertebral body 42.

Once the superior endplate 46 has been restored to the desired position and the volume of trabecular bone 48 has been reduced, device 10*a* is withdrawn from the interior volume of the vertebral body 42. Preferably, blades 26 are returned to their unexpanded state prior to removal of device 10*a*. After removal of device 10*a*, a biological binding material is instilled into the vertebral body 42. As used herein, a biological binding material is any material suitable for placement in an internal portion of a bone in a human body and that is capable of providing stability and/or added strength to such a bone. Preferably, the biological binding material is also capable of interdigitating with internal surfaces of a bone, such as trabecular bone. Examples of biological binding materials include, but are not limited to, cements containing polymethylmethacrylate (PMM) and materials utilizing biological or synthetic bone. The preferred biological binding material is a cement that contains PMM. In some embodiments, the biological binding material may contain additional substances, such as antibiotics or compounds that aid imaging of the biological binding material once it is added to the body. In some embodiments, the biological binding material may contain barium to aid fluoroscopic imaging of the biological binding material.

The biological binding material may be instilled into the vertebral body by any suitable method using any suitable device. Preferably, the biological binding material is instilled through the cannula 60 and into the vertebral body 42, as is known in the art. Any amount of biological binding material sufficient to add stability to vertebral body 42 may be used. Preferably, biological binding material is added until vertebral body 42, including the void created by device 10*a*, is filled. In preferred embodiments where trabecular bone 48 has been cut, carved, or shaved, the biological binding material may interdigitate with the exposed trabecular bone 48. In such embodiments, the interdigitation of the biological binding material and the trabecular bone 48 forms a bond that is capable of maintaining the restored vertebral height even after the subsequent placement of mechanical loading on the spine.

It is seen that devices and methods are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example configuration for the invention, which is done to aid in understanding the features and functionality that may be included in the invention. The invention is not restricted to the illustrated example configurations, but the desired features may be implemented using a variety of alternative configurations. Indeed, it will be apparent to one of skill in the art how alternative functional or physical configurations may be implemented to implement the desired features of the present invention. Additionally, with regard to operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary illustrations and figures. As will become apparent to one of ordinary skill in the art after reading this document, the illustrated embodiments and their various alternatives may be implemented without confinement to the illustrated examples.

The invention claimed is:

1. A device for stabilizing compression fractures of the spine comprising:
   a housing having a lumen with a threaded track disposed along at least a portion of the lumen;
   a plunger having a proximal portion and a distal portion, wherein the plunger is disposed within the lumen and is movable relative to the housing, and wherein the plunger comprises a threaded portion that mates with the threaded track of the lumen of the housing;
   a plurality of blades located at the distal portion of the plunger, wherein a proximal end of each of the plurality of blades is coupled to a distal end of the plunger, and a distal end of each of the plurality of blades is coupled to the housing, and wherein the blades are configured to:
      expand convexially by bowing outward from an axis of the housing; and
      reduce a volume of trabecular bone within a vertebral body of the spine by cutting through the volume while rotating about the axis of the housing; and
   a manipulator functionally connected to the plunger, wherein the manipulator is configured to bend the blades convexially from the axis of the housing while the manipulator rotates the blades about the axis of the housing using the threaded track.

2. The device of claim 1, wherein the plurality of blades is two blades.

3. The device of claim 1, wherein the plurality of blades is three blades.

4. The device of claim 1, wherein the plurality of blades is six blades.

5. The device of claim 1, wherein the plurality of blades bend to a plurality of diameters.

6. The device of claim 5, wherein the manipulator is further operable to expand the plurality of blades to a plurality of diameters.

7. The device of claim 1, wherein the device is employed to access an internal volume of the vertebral body.

8. The device of claim 7, wherein a biological binding material is introduced into the internal volume of the vertebral body.

9. The device of claim 1, wherein the device is further employed to restore the height of a superior endplate of the vertebral body to a normal anatomical position.

10. A kit comprising:
    the device of claim 1;
    a large-bore cannula;
    PMM cement; and
    a device operable to deliver the cement to an internal volume of a bone.

11. The device of claim 1, wherein the plurality of blades are operable to reduce the volume of trabecular bone by cutting trabecular bone to create a space in the vertebral body.

12. The device of claim 1, wherein the housing has a plurality of slots located close to a distal end of the housing.

* * * * *